(12) United States Patent
Tsuji et al.

(10) Patent No.: US 6,339,162 B1
(45) Date of Patent: Jan. 15, 2002

(54) PROCESS FOR THE PREPARATION OF TETRAHYDROPYRAN DERIVATIVES

(75) Inventors: Masahiro Tsuji; Hiroyuki Yamazaki, both of Saitama-ken (JP)

(73) Assignee: Nisshin Pharma Inc., Tokyo (JP)

( * ) Notice: Subject to any disclaimer, the term of this patent is extended or adjusted under 35 U.S.C. 154(b) by 0 days.

(21) Appl. No.: 09/531,423

(22) Filed: Mar. 20, 2000

(30) Foreign Application Priority Data

Mar. 29, 1999 (JP) ............................. 11-085999

(51) Int. Cl.⁷ ...................... C07D 309/06; C07D 309/10

(52) U.S. Cl. ........................................ 549/418; 549/421

(58) Field of Search .................................. 549/418, 421

(56) References Cited

FOREIGN PATENT DOCUMENTS

| GB | 394195 | 6/1933 |
| JP | 62-226974 | 10/1987 |
| WO | WO 97/49716 | 12/1997 |

OTHER PUBLICATIONS

[19] Migration of Expoxide Rings and Stereoselective Ring Opening of Acetoxyepoxides, J. G. Buchanan, 1972, Academic Press, Whistler R. L. and Wolfrom M. L., Eds., vol. VI, New York, pp. 135–140.

"[41] D–Idose", L. F. Wiggins, 1962, Academic Press, Whistler R. L. and Wolfrom M. L., Eds., vol. 1, New Yhork, pp. 140–143.

"Carbohydrate Laboratory Techniques [1] Removal of Inorganic Material from Solution", A. Thompson et al., 1962, Academic Press, Whistler R. L. and Wolfrom M. L. Eds., vol. I, New York, p. 3.

*Primary Examiner*—Tarofiq Solola
(74) *Attorney, Agent, or Firm*—McDermott, Will & Emery

(57) ABSTRACT

A process of making arbutin and its derivatives comprises solvolyzing an acylated precursor of arbutin or its derivative in a solution comprising an organic solvent and a base, neutralizing the solution with an acid, and crystillizing the product arbutin or its derivative. The process may be employed on an industrial scale and avoids the use of ion exchange columns. The process has the advantages of not requiring ion exchange columns and peripheral devices, which leads to cost and time savings, due to the elimination of column regeneration steps. Waste water from column regeneration is also eliminated.

6 Claims, No Drawings

PROCESS FOR THE PREPARATION OF TETRAHYDROPYRAN DERIVATIVES

FIELD OF THE INVENTION

This invention relates to an improved process for the preparation of arbutin or its derivatives which are useful as raw materials for industrial chemicals, medicines and cosmetics. More particularly, the invention relates to an efficient process for preparing tetrahydropyran derivatives on an industrial scale.

BACKGROUND OF THE INVENTION

A variety of methods have been known as processes for the preparation of 4-hydroxyphenyl-β-D-glucopyranoside represented by the following formula, i.e., arbutin.

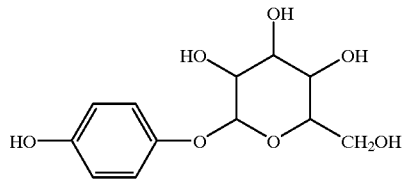

These known methods require a treatment to remove acyl groups by hydrolysis in an aqueous solvent from an intermediate wherein hydroxyl groups in the glucopyranoside are acylated. This hydrolysis is carried out in the presence of a base such as sodium hydroxide, potassium hydroxide and sodium methylate. In this process, any inorganic cation forming during the hydrolysis may contaminate the object product. Japanese Patent Kokai 62-226974 proposes a method of treating the reaction solution after hydrolysis with a cation exchange resin to avoid the contamination.

However, a method for preparing arbutin or its derivatives by using a cation exchange resin on an industrial scale has the following problems.

i) Increase in number of ion-exchange columns and peripheral equipments requires more installation places, resulting in increased cost of the equipments.
ii) Regeneration treatment of ion exchange resins is time-consuming.
iii) Much volume of washing water used for the regeneration brings about increased volume of drainage.

In the circumstances, there is still a demand for an efficient process for the preparation of arbutin or its derivatives on an industrial scale.

As a result of studying the above-mentioned problems, the present inventors have found that the tetrahydropyran derivatives of the following formula (II) can be easily prepared on an industrial scale by solvolyzing in an organic solvent a compound of the following formula (I) in the presence of a base, followed by neutralizing with an acid, and crystallizing.

Thus the present invention provides a process for the preparation of a tetrahydropyran derivative of formula (II)

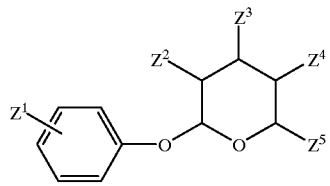

wherein $Z^1$, $Z^2$, $Z^3$, $Z^4$ and $Z^5$ have respectively the same meaning as defined below for $R^1$, $R^2$, $R^3$, $R^4$ and $R^5$, provided that a $C_1$–$C_4$ alkylcarbonyloxy group in formula (I) is converted into a hydroxyl group, and a $C_1$–$C_4$ alkylcarbonyloxy $C_1$–$C_4$ alkyl group is converted into a hydroxyl $C_1$–$C_4$ alkyl group, which comprises solvolyzing in an organic solvent a compound of formula (I)

(I)

wherein $R^1$, $R^2$, $R^3$ and $R^4$ may be the same or different, and each represents a hydrogen atom, a hydroxyl group, a $C_1$–$C_4$ alkoxy group, a $C_1$–$C_4$ alkylcarbonyloxy group or an aryl $C_1$–$C_4$ alkyloxy group, and $R^5$ represents a hydrogen atom, a $C_1$–$C_4$ alkyl group, a hydroxy $C_1$–$C_4$ alkyl group or a $C_1$–$C_4$ alkylcarbonyloxy $C_1$–$C_4$ alkyl group, provided that at least one of $R^1$, $R^2$, $R^3$ and $R^4$ is a $C_1$–$C_4$ alkylcarbonyloxy group, in the presence of a base, followed by neutralizing with an acid and crystallizing.

In formulae (I) and (II),
 a $C_1$–$C_4$ alkyl group includes methyl, ethyl, propyl, isopropyl, butyl, sec-butyl and tert-butyl;
 a $C_1$–$C_4$ alkoxy group includes methoxy, ethoxy, propoxy, isopropoxy, butoxy, sec-butoxy and tert-butoxy;
 a $C_1$–$C_4$ alkylcarbonyloxy group includes acetyloxy, propionyloxy, butyryloxy, isobutyryloxy, valeryloxy, isovaleryloxy group and the like;
 an aryl $C_1$–$C_4$ alkyloxy group includes a phenyl $C_1$–$C_4$ alkyloxy, e.g., benzyloxy, phenethyloxy and the like;
 a hydroxy $C_1$–$C_4$ alkyl group includes hydroxymethyl, 2-hydroxyethyl, 3-hydroxypropyl, 2-hydroxy-1-methylethyl, 4-hydroxybutyl and the like; and
 a $C_1$–$C_4$ alkylcarbonyloxy $C_1$–$C_4$ alkyl group includes acetyloxymethyl, 2-acetyloxyethyl, 3-acetyloxypropyl, 4-acetyloxybutyl, propionyloxymethyl, 2-propionyloxyethyl, 3-propionyloxypropyl, 4-propionyloxybutyl, butyryloxymethyl, 2-butyryloxyethyl, 3-butyryloxypropyl, isobutyryoxymethyl, 2-isobutyryoxyethyl, valeryloxymethyl, 2-valeryloxyethyl, 3-valeryloxypropyl and the like.

Illustrative examples of compounds of formula (I) include 4-acetyloxyphenyl-2,3,4,6-tetra-O-acetyl-β-D-glucopyranoside, 4-hydroxyphenyl-2,3,4,6-tetra-O-acetyl-β-D-glucopyranoside, 4-methoxyphenyl-2,3,4,6-tetra-O-acetyl-β-D-glucopyranoside, 4-benzyloxyphenyl-2,3,4,6-tetra-O-acetyl-β-D-glucopyranoside, 4-acetyloxyphenyl-2,3,4,6-tetra-O-acetyl-β-D-galactopyranoside, phenyl-2,3,4, 6-tetra-O-acetyl-β-D-glucopyranoside, phenyl-2,3,4,6-tetra-O-acetyl-β-D-galactopyranoside and the like.

Illustrative examples of compounds of formula (II) include 4-hydroxyphenyl-β-D-glucopyranoside (arbutin), 4-methoxyphenyl-β-D-glucopyranoside, phenyl-β-D-glucopyranoside, 4-hydroxyphenyl-β-D-galactopyranoside, phenyl-β-D-galactopyranoside, 4-benzyloxyphenyl-β-D-glucopyranoside and the like.

The tetrahydropyran derivatives of formula (II) can be prepared by solvolyzing in an organic solvent the compound of formula (I) in the presence of a base, followed by neutralization and purification by crystallization, with no use of an ion exchange resin which has been used in the prior art. In this case, a concentration of salts forming by neutralization is adjusted to a level at which arbutin or its derivatives are soluble in a crystallization solvent, by appropriately controlling kinds and amounts of bases used in solvolysis and kinds and amounts of acids used in neutralization.

This operation enables the preparation of arbutin or its derivatives in high yield with no use of special purification means such as an ion exchange.

The temperature in solvolysis is in the range from room temperature to the boiling point of a solvent, preferably the boiling point of the solvent used. The time required for solvolysis depends on raw materials, bases, solvents and the like, but is usually within the range from one hour to 24 hours.

Bases used in the present invention include hydroxides such as sodium hydroxide, potassium hydroxide and the like, alcoholates such as sodium methylate, sodium ethylate, potassium t-butylate and the like. An amount of bases used ranges from 1 mol % to 20 mols % based on the compound of formula (I). Acids used for neutralizing bases include organic acids such as formic acid, acetic acid, p-toluenesulfonic acid, methanesulfonic acid and the like. As an organic solvent, alcohols can be used such as methanol, ethanol and the like. The solubility of a salt in each solvent (100 g) is, for example, in the case of sodium acetate, 4.51 g in ethanol at room temperature and 16.00 g in methanol at 15° C., and in the case of sodium formate, 3.52 g in methanol at 15° C.

The present invention is further illustrated by the following non-limiting examples.

EXAMPLE 1

To 4-acetyloxyphenyl-2,3,4,6-tetra-O-acetyl-β-D-glucopyranoside (28.0 g) were added methanol (140 ml) and 28% sodium methylate (0.28 ml) and the mixture was refluxed with stirring for 4 hours. After the reaction solution was cooled, acetic acid (0.1 ml) was added and the mixture was stirred for 30 minutes. Concentration of the reaction solution and crystallization with ethanol (200 ml) gave 12.8 g (yield 81%) of arubutin.

Melting point: 199.6° C.

EXAMPLE 2

To 4-hydroxyphenyl-2,3,4,6-tetra-O-acetyl-β-D-glucopyranoside (20.0 g) were added methanol (100 ml) and 28% sodium methylate (0.17 ml) and the mixture was refluxed with stirring for 4 hours. After the reaction solution was cooled, acetic acid (0.07 ml) was added and the mixture was stirred for 30 minutes. Concentration of the reaction solution and crystallization with ethanol (140 ml) gave 9.9 g (yield 80%) of arubutin.

EXAMPLE 3

To 4-acetyloxyphenyl-2,3,4,6-tetra-O-acetyl-β-D-glucopyranoside (24.1 g) were added methanol (120 ml) and sodium hydroxide (0.2 g) and the mixture was refluxed with stirring for 5 hours. After the reaction solution was cooled, acetic acid (0.3 ml) was added and the mixture was stirred for 30 minutes. Concentration of the reaction solution and crystallization with ethanol (180 ml) gave 10.9 g (yield 80%) of arubutin.

EXAMPLE 4

To 4-acetyloxyphenyl-2,3,4,6-tetra-O-acetyl-β-D-glucopyranoside (24.1 g) were added methanol (120 ml) and potassium hydroxide (0.3 g) and the mixture was refluxed with stirring for 5 hours. After the reaction solution was cooled, acetic acid (0.3 ml) was added and the mixture was stirred for 30 minutes. Concentration of the reaction solution and crystallization with ethanol (180 ml) gave 10.5 g (yield 77%) of arubutin.

EXAMPLE 5

To 4-acetyloxyphenyl-2,3,4,6-tetra-O-acetyl-β-D-glucopyranoside (24.1 g) were added methanol (120 ml) and sodium hydroxide (0.1 g) and the mixture was refluxed with stirring for 7 hours. After the reaction solution was cooled, formic acid (0.1 ml) was added and the mixture was stirred for 30 minutes. Concentration of the reaction solution and crystallization with ethanol (180 ml) gave 10.7 g (yield 79%) of arubutin.

EXAMPLE 6

To 4-acetyloxyphenyl-2,3,4,6-tetra-O-acetyl-β-D-galactopyranoside (28.0 g) were added methanol (140 ml) and 28% sodium methylate (0.28 ml), and the mixture was refluxed with stirring for 4 hours. After the reaction solution was cooled, acetic acid (0.1 ml) was added and the mixture was stirred for 30 minutes. Concentration of the reaction solution and crystallization with ethanol (180 ml) gave 11.8 g (yield 75%) of arubutin.

EXAMPLE 7

To phenyl-2,3,4,6-tetra-O-acetyl-β-D-glucopyranoside (21.2 g) were added methanol (120 ml) and 28% sodium methylate (0.28 ml) and the mixture was refluxed with stirring for 5 hours. After the reaction solution was cooled, acetic acid (0.1 ml) was added and the mixture was stirred for 30 minutes. Concentration of the reaction solution and crystallization with ethanol (180 ml) gave 10.0 g (yield 78%) of phenyl-β-D-glucopyranoside. Melting point: 177.0° C.

EXAMPLE 8

To phenyl-2,3,4,6-tetra-O-acetyl-β-D-galactopyranoside (21.2 g) were added methanol (120 ml) and 28% sodium methylate (0.28 ml) and the mixture was refluxed with stirring for 5 hours. After the reaction solution was cooled, acetic acid (0.1 ml) was added and the mixture was stirred for 30 minutes. Concentration of the reaction solution and crystallization with ethanol (180 ml) gave 9.8 g (yield 77%) of phenyl-β-D-galactopyranoside. Melting point: 154.5° C.

EXAMPLE 9

To 4-methoxyphenyl-2,3,4,6-tetra-O-acetyl-S-D-glucopyranoside (22.7 g) were added methanol (120 ml) and 28% sodium methylate (0.28 ml) and the mixture was refluxed with stirring for 5 hours. After the reaction solution was cooled, acetic acid (0.1 ml) was added and the mixture was stirred for 30 minutes. Concentration of the reaction solution and crystallization with ethanol (180 ml) gave 11.2 g (yield 78%) of 4-methoxyphenyl-β-D-glucopyranoside.

Melting point: 160.0° C.

What is claimed is:

1. A process of preparing a compound of formula (II):

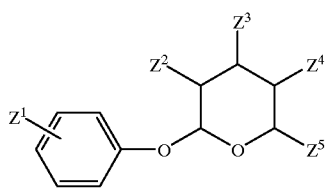

(II)

wherein each of $Z^1$, $Z^2$, $Z^3$ and $Z^4$ is independently a hydrogen atom, a hydroxyl group, a $C_1$–$C_4$ alkoxy group or an aryl $C_1$–$C_4$ alkyloxy group, and $Z^5$ represents a hydrogen atom, a $C_1$–$C_4$ alkyl group or a hydroxyl $C_1$–$C_4$ alkyl group, with the proviso that at least one of $Z^1$–$Z^4$ is a hydroxyl or $Z^5$ is a hydroxyl $C_1$–$C_4$ alkyl group, the process comprising: solvolyzing, in an organic solvent, in the presence of a base, a compound of formula (I):

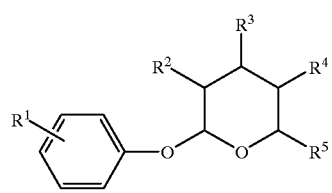

(I)

wherein $R^1$, $R^2$, $R^3$, and $R^4$ are the same or different, and each represents a hydrogen atom, a hydroxyl group, a $C_1$–$C_4$ alkoxy group, a $C_1$–$C_4$ alkylcarbonyloxy group or an aryl $C_1$–$C_4$ alkyloxy group, and $R^5$ represents a hydrogen atom, a $C_1$–$C_4$ alkyl group, a hydroxyl $C_1$–$C_4$ alkyl group or a $C_1$–$C_4$ alkylcarbonyloxy $C_1$–$C_4$ alkyl group, provided that at least one of the following conditions is met with respect to $R^1$–$R^5$: at least one of $R^1$, $R^2$, $R^3$ and $R^4$ is a $C_1$–$C_4$ alkylcarbonyloxy group, or $R^5$ is a $C_1$–$C_4$ alkylcarbonyloxy $C_1$–$C_4$ alkyl group; whereby at least one of $R^1$, $R^2$, $R^3$ or $R^4$, being said $C_1$–$C_4$ alkylcarbonyloxy group, is hydrolyzed to form a hydroxyl group, or $R^5$, being said $C_1$–$C_4$ alkylcarbonylcarbonyloxy $C_1$–$C_4$ alkyl group, is hydrolyzed to form a hydroxyl $C_1$–$C_4$ alkyl group;

followed by neutralizing with an acid, and then crystallizing the compound having formula (II).

2. The process of claim 1, wherein each of $R^1$, $R^2$, $R^3$ and $R^4$ is a $C_1$–$C_4$ alkylcarbonyloxy group and $R^5$ is a $C_1$–$C_4$ alkyl group.

3. The process of claim 1, wherein $R^1$ is a hydrogen atom or a hydroxyl group, each of $R^2$, $R^3$ and $R^4$ is a $C_1$–$C_4$ alkylcarbonyloxy group and $R^5$ is a hydroxyl $C_1$–$C_4$ alkyl group.

4. The process of claim 1, wherein $R^1$ is a $C_1$–$C_4$ alkyloxy group, each of $R^2$, $R^3$ and $R^4$ is a $C_1$–$C_4$ alkylcarbonyloxy group and $R^5$ is a hydroxyl $C_1$–$C_4$ alkyl group.

5. The process of claim 1, wherein $R^1$ is an aryl $C_1$–$C_4$ alkyloxy group, each of $R^2$, $R^3$ and $R^4$ is a $C_1$–$C_4$ alkylcarbonyloxy group and $R^5$ is a hydroxyl $C_1$–$C_4$ alkyl group.

6. The process of claim 1, wherein $R^5$ is a hydroxymethyl group.

* * * * *